United States Patent
Zhang et al.

(10) Patent No.: US 12,203,935 B2
(45) Date of Patent: Jan. 21, 2025

(54) PROBE FOR UNIVERSAL DETECTION OF CIRCULATING TUMOR CELLS

(71) Applicant: The University of Houston System, Houston, TX (US)

(72) Inventors: Shaun Xiaoliu Zhang, Houston, TX (US); Xinping Fu, Houston, TX (US)

(73) Assignee: The University of Houston System, Houston, TX (US)

( * ) Notice: Subject to any disclaimer, the term of this patent is extended or adjusted under 35 U.S.C. 154(b) by 1068 days.

(21) Appl. No.: 16/970,163

(22) PCT Filed: Feb. 14, 2019

(86) PCT No.: PCT/US2019/018120
§ 371 (c)(1),
(2) Date: Aug. 14, 2020

(87) PCT Pub. No.: WO2019/161139
PCT Pub. Date: Aug. 22, 2019

(65) Prior Publication Data
US 2021/0102946 A1 Apr. 8, 2021

Related U.S. Application Data

(60) Provisional application No. 62/630,570, filed on Feb. 14, 2018.

(51) Int. Cl.
*G01N 33/574* (2006.01)
*C12N 15/86* (2006.01)
*C12Q 1/66* (2006.01)
*G01N 33/50* (2006.01)

(52) U.S. Cl.
CPC .......... *G01N 33/574* (2013.01); *C12N 15/86* (2013.01); *C12Q 1/66* (2013.01); *G01N 33/5091* (2013.01); *C12N 2710/22031* (2013.01); *C12N 2710/22043* (2013.01)

(58) Field of Classification Search
None
See application file for complete search history.

(56) References Cited

U.S. PATENT DOCUMENTS

| | | |
|---|---|---|
| 2017/0121688 A1 | 5/2017 | Gil et al. |
| 2017/0298454 A1 | 10/2017 | Dorsey et al. |
| 2017/0335292 A1 | 11/2017 | Dumas et al. |

FOREIGN PATENT DOCUMENTS

| | | |
|---|---|---|
| JP | 2005538731 A | 12/2005 |
| JP | 2016531591 A | 10/2016 |
| WO | 2008140961 A2 | 11/2008 |

OTHER PUBLICATIONS

Liu Y, Frazer IH, Liu WJ, Liu XS, McMillan N, Zhao KN. Efficiency of delivery of DNA to cells by bovine papillomavirus type-1 L1/L2 pseudovirions. Appl Microbiol Biotechnol. Jul. 2001;56(1-2):150-6. doi: 10.1007/s002530100655. PMID: 11499923.*
Liu Y, Frazer IH, Liu WJ, Liu XS, McMillan N, Zhao KN. Efficiency of delivery of DNA to cells by bovine papillomavirus type-1 L1/L2 pseudovirions. Appl Microbiol Biotechnol. Jul. 2001;56(1-2):150-6. doi: 10.1007/s002530100655. PMID: 11499923. (Year: 2001).*
Kines RC, Cerio RJ, Roberts JN, Thompson CD, de Los Pinos E, Lowy DR, Schiller JT. Human papillomavirus capsids preferentially bind and infect tumor cells. Int J Cancer. Feb. 15, 2016;138(4):901-11. doi: 10.1002/ijc.29823. Epub Oct. 27, 2015. PMID: 26317490. (Year: 2016).*
Hojeij, et al. Int J Mol Sci. Jul. 14, 2016;17(7):1125. doi: 10.3390/ijms17071125. PMID: 27428950. (Year: 2016).*
Nandi, et al. Mol Cell Biol. Mar. 1985;5(3):591-4. doi: 10.1128/mcb.5.3.591-594.1985. PMID: 2985959. (Year: 1985).*
Extended Search Report mailed Nov. 11, 2021 issued in counterpart European Patent Application No. 19753988.5.
Tillig, Thore et al. "In Vitro Detection of circulating tumor cells compared by the CytoTrack and CellSearch methods." Tumor Biol. (2015) 36:4597-4601. DOI 10.1007/s13277-015-3105-z. pp. 4597-4601.
Fu, Xinping et al. "A chimeric virus-based probe unambiguously detects live circulating tumor cells with high specificity and sensitivity." Molecular Therapy—Methods & Clinical Development, vol. 23, Aug. 28, 2021. pp. 78-86.
Aksoy, et al., "HPV entry into cells," Mutat. Res. 772, 2017.
Andree, et al., "Challenges in circulating tumor cell detection by the CellSearch system," Molecular Oncology 10, 2016.
Brady, et al., "Simian Virus 40 Major Late Promoter: an Upstream DNA Sequence Required for Efficient In Vitro Transcription," Molecular and Cellular Biology, Jan. 1984.
Buck, et al., "Arrangement of L2 within the Papillomavirus Capsid," Journal of Virology vol. 82, No. 11, Jun. 2008.
Buck, et al., "Efficient Intracellular Assembly of Papillomaviral Vectors," Journal of Virology vol. 78, No. 2, Jan. 2004.
Chebel, "Transcriptional Activation of hTERT, the Human Telomerase Reverse Transcriptase, by Nuclear Factor of Activated T Cells," The Journal of Biological Chemistry, vol. 284, No. 51, Dec. 18, 2009.
Coumans, et al., "Challenges in the Enumeration and Phenotyping of CTC," Clinical Cancer Research 18(20), Oct. 15, 2020.
Dotan, et al., "Circulating Tumor Cells: Evolving Evidence and Future Challenges," Oncologist 14(11), Nov. 2009.
Fu, et al., "A Mutant Type 2 Herpes Simplex Virus Deleted for the Protein Kinase Domain of the ICP10 Gene Is a Potent Oncolytic Virus," Molecular Therapy vol. 13, No. 5, May 2006.
Fu, et al., "Expression of a Fusogenic Membrane Glycoprotein by an Oncolytic Herpes Simplex Virus Potentiates the Viral Antitumor Effect," Molecular Therapy vol. 7, No. 6, Jun. 2003.
Gorges, et al., "Circulating tumour cells escape from EpCAM-based detection due to epithelial-to-mesenchymal transition," BMC Cancer 12:178, 2012.

(Continued)

*Primary Examiner* — Benjamin P Blumel
*Assistant Examiner* — Jeffrey Mark Sifford
(74) *Attorney, Agent, or Firm* — Blank Rome LLP

(57) ABSTRACT

Disclosed are probes based on papilloma virus and modified SV40 that can be used for detecting circulating tumor cells (CTCs) in the blood stream, methods for manufacturing such probes, and methods for using such probes.

14 Claims, 9 Drawing Sheets

Specification includes a Sequence Listing.

(56) References Cited

OTHER PUBLICATIONS

Hojeij, et al., "Immunogenic Human Papillomavirus Pseudovirus-Mediated Suicide-Gene Therapy for Bladder Cancer," International Journal of Molecular Sciences 17, 1125, 2016.

Hvichia, "A novel microfluidic platform for size and deformability based separation and the subsequent molecular characterization of viable circulating tumor cells," International Journal of Cancer 138(12), 2016.

Kines, et al., "Human papillomavirus capsids preferentially bind and infect tumor cells," International Journal of Cancer 138, 2016.

Lednicky, "Simian virus 40 regulatory region structural diversity and the association of viral archetypal regulatory regions with human brain tumors," Cancer Biology vol. 11, 2001.

Lin, et al., "Portable Filter-Based Microdevice for Detection and Characterization of Circulating Tumor Cells," Clinical Cancer Research 16(20), Oct. 15, 2010.

Liu, et al., "Efficiency of delivery of DNA to cells by bovine papillomavirus type-1 L1/L2 pseudovirions," Appl. Microbiol. Biotechnol. 56, 2001.

Nandi, et al., "Characterization of a Surrogate TATA Box Promoter That Regulates In Vitro Transcription of the Simian Virus 40 Major Late Gene," Molecular and Cellular Biology vol. 5, No. 3, Mar. 1985.

Pantel, Klaus, and Catherine Alix-Panabieres, "Circulating tumour cells in cancer patients: challenges and perspectives," Trends in Molecular Medicine 16 (2010).

International Search Report and Written Opinion received in International Application No. PCT/US2019/018120, mailed Oct. 1, 2019.

Plaeger-Marshall, et al., "Replication of Herpes Simplex Virus in Blood Monocytes and Placental Macrophages from Human Neonates," Pediatric Research vol. 26, No. 2, 1989.

Pollara, et al., "Herpes Simplex Virus Infection of Dendritic Cells: Balance among Activation, Inhibition, and Immunity," The Journal of Infectious Diseases 187, 2003.

Posavad, et al., "Infection and Inhibition of Human Cytotoxic T Lymphocytes by Herpes Simplex Virus," Journal of Virology vol. 68, No. 6, Jun. 1994.

Raftery, et al., "Herpes Simplex Virus Type 1 Infection of Activated Cytotoxic T Cells: Induction of Fratricide as a Mechanism of Viral Immune Evasion," J. Exp. Med. Vol. 190, No. 8, Oct. 18, 1999.

Riethdorf, et al., "Detection of Circulating Tumor Cells in Peripheral Blood of Patients with Metastatic Breast Cancer: A Validation Study of the CellSearch System," Clinical Cancer Research 13(3), Feb. 1, 2007.

Rosenberg, et al., "Comparison of Two Density Gradient Centrifugation Systems for the Enrichment of Disseminated Tumor Cells in Blood," Cytometry 49, 2002.

Simmons, Daniel T., "SV40 Large T Antigen Functions in DNA Replication and Transformation," Advances in Virus Research vol. 55, 2000.

Vona, et al., "Isolation by Size of Epithelial Tumor Cells: A New Method for the Immunomorphological and Molecular Characterization of Circulating Tumor Cells," American Journal of Pathology vol. 156, No. 1, Jan. 2000.

Wiley, et al., "SV40 early-to-late switch involves titration of cellular transcriptional repressors," Genes & Development 7, 1993.

Zhang, et al., "The prognostic and diagnostic value of circulating tumor cells in bladder cancer and upper tract urothelial carcinoma: a meta-analysis of 30 published studies," Oncotarget vol. 8, No. 35, Jun. 16, 2017.

Zhang, et al., "Tumor-selective replication herpes simplex virus-based technology significantly improves clinical detection and prognostication of viable circulating tumor cells," Ocotarget, 2016.

Encell, L. et al., Definition: Nanoluc IL6 (secNluc) reporter [Nanoluc luciferase reporter vector pNL1.3[secNluc]]. Database GenBank[online], Accession No. AFI79293.1 <https://urldefense.com/v3/_https://www.ncbi.nlm.nih.gov/protein/AFI79293.1/.

* cited by examiner

SEQUENCE LISTING

```
<160> NUMBER OF SEQ ID NOS: 13

<210> SEQ ID NO 1
<211> LENGTH: 743
<212> TYPE: DNA
<213> ORGANISM: Simian virus 40
<220> FEATURE:
<221> NAME/KEY: extra 4 x 72 base pair (bp) tandem repeat enhancer
      sequence
<222> LOCATION: (330)..(617)
<220> FEATURE:
<221> NAME/KEY: mutated nucleotides at number 671 from C to T
<222> LOCATION: (671)..(671)
<220> FEATURE:
<221> NAME/KEY: mutated nucleotides at number 672 from C to T
<222> LOCATION: (672)..(672)
<220> FEATURE:
<221> NAME/KEY: mutated nucleotides at number 677 from C to T
<222> LOCATION: (677)..(677)
<220> FEATURE:
<221> NAME/KEY: mutated nucleotides at number 695 from G to C
<222> LOCATION: (695)..(695)
<220> FEATURE:
<221> NAME/KEY: mutated nucleotides at number 708 from C to A
<222> LOCATION: (708)..(708)
```

<400> SEQUENCE: 1

```
aagcttttg caaaagccta ggcctccaaa aaagcctcct cactacttct ggaatagctc      60
agaggccgag gcggcctcgg cctctgcata aataaaaaaa attagtcagc catgggggcgg    120
agaatgggcg gaactgggcg gagttagggg cgggatgggc ggagttaggg gcgggactat    180
ggttgctgac taattgagat gcatgctttg catacttctg cctgctgggg agcctgggga    240
ctttccacac ctggttgctg actaattgag atgcatgctt tgcatacttc tgcctgctgg    300
ggagcctggg gactttccac accactagtt ggttgctgac taattgagat gcatgctttg    360
catacttctg cctgctgggg agcctgggga ctttccacac ctggttgctg actaattgag    420
atgcatgctt tgcatacttc tgcctgctgg ggagcctggg gactttccac acctggttgc    480
tgactaattg agatgcatgc tttgcatact tctgcctgct ggggagcctg ggacttttcc    540
acacctggtt gctgactaat tgagatgcat gctttgcata cttctgcctg ctggggagcc    600
tggggacttt ccacaccact agtctaactg acacacattc cacagctggt tctttccgcc    660
tcagaaggta tttaactaag ttcctctttc agagcttatt tcaggccctg gtgctgcgcc    720
ggctgtcacg ccaggcctcc gtt                                             743
```

<210> SEQ ID NO 2
<211> LENGTH: 2473
<212> TYPE: DNA
<213> ORGANISM: Simian virus 40

<400> SEQUENCE: 2

```
atggacaagg tgctgaaccg ggaggagagc ctgcagctga tggatctgct gggcctggag      60
cggtccgcct ggggaaatat ccccctgatg agaaaggcct acctgaagaa gtgcaaggag    120
ttccaccctg acaagggcgg cgatgaggag aagatgaaga gatgaacac cctgtataag    180
aagatggagg acggcgtgaa gtatgcccac cagcccgact ttggaggctt ctgggatgca    240
actgaggtat ttgcttcttc cttaaatcct ggtgttgatg caatgtactg caaacaatgg    300
cctgagtgtg caaagaaaat gtctgctaac tgcatatgct tgctgtgctt actgaggatg    360
aagcatgaaa atagaaaatt atacaggaaa gatccacttg tgtgggttga ttgctactgc    420
ttcgattgct ttagaatgtg gtttggactt gatctttgtg aaggaacctt acttctgtgg    480
tgtgacataa ttgacaaaac tacctacaga gatttaaagc tctaaggtaa atataaaatt    540
tttaagtgta taatgtgtta aactactgat tctaattgtt tgtgtatttt agattccaac    600
ctatggaact gatgaatggg agcagtggtg gaatgccttt aatgaggaaa acctgttttg    660
ctcagaagaa atgccaagct ccgacgatga ggccaccgcc gactctcagc acagcacacc    720
ccccaagaag aagcggaagg tggaggaccc caaggatttc ccttccgagc tgctgtcctt    780
cctgtctcac gccgtgtttt ctaacaggac cctggcctgc tttgccatct acaccacaaa    840
ggagaaggcc gccctgctgt ataagaagat catggagaag tatagcgtga ccttcatctc    900
ccgccacaat tcttacaacc acaatatcct gttctttctg acaccccacc ggcacagagt    960
gagcgccatc aacaattatg cccagaagct gtgcaccttc cctttctga tctgtaaggg   1020
cgtgaacaag gagtacctga tgtatagcgc cctgacacgg gaccccttca gcgtgatcga   1080
ggagtccctg ccaggaggcc tgaaggagca cgactttaat cccgaggagg ccgaggagac   1140
caagcaggtg tcctggaagc tggtgaccga gtacgctatg gagacaaagt gcgacgatgt   1200
gctgctgctg ctgggcatgt acctggagtt ccagtattct tttgagatgt gcctgaagtg   1260
tatcaagaag gagcagccta gccactacaa gtatcacgag aagcactatg ccaacgccgc   1320
```

```
catctttgcc gattccaaga atcagaagac aatctgtcag caggccgtgg ataccgtgct    1380
ggccaagaag agagtggact ctctgcagct gaccaggggag cagatgctga caaaccgctt    1440
caatgacctg ctggatcgga tggacatcat gtttggcagc accggctccg ccgacatcga    1500
ggagtggatg caggagtgg catggctgca ctgcctgctg cccaagatgg atagcgtggt    1560
gtacgacttc ctgaagtgta tggtgtataa catccccaag aagcggtact ggctgtttaa    1620
gggcccaatc gattccggca agaccacact ggccgccgcc ctgctggagc tgtgcgaggg    1680
caaggccctg aacgtgaatc tgcctctgga ccggctgaac ttcgagctgg cgtggccat    1740 cgatcagttc ctggtggtgt ttgaggacgt gaagggcaca ggaggagagt ctcgcgatct    1800
gccaagcgga cagggcatca acaatctgga caacctgcgg gattatctgg acggctctgt    1860
gaaggtgaac ctggagaaga agcacctgaa taagaggaca cagattttcc cacccggcat    1920
cgtgaccatg aatgagtact ccgtgccaaa gacactgcag gcccgcttcg tgaagcagat    1980
cgattttcgg cccaaggact atctgaagca ctgtctggag agatccgagt tcctgctgga    2040
gaagaggatc atccagagcg gcatcgccct gctgctgatg ctgatctggt acagacctgt    2100
ggccgagttt gcccagtcta tccagagcag aatcgtggag tggaaggaga ggctggataa    2160
ggagttctcc ctgagcgtgt accagaagat gaagtttaac gtggctatgg gcatcggcgt    2220
gctggattgg ctgcggaaca cgacgatga cgatgaggac tctcaggaga acgccgataa    2280
gaatgaggac ggcggcgaga agaacatgga ggatagcggc cacgagaccg gcatcgacag    2340
ccagtcccag ggcagcttcc aggcaccaca gtctagccag tccgtgcacg accacaatca    2400
gccttaccac atctgccggg gcttcacctg tttttaagaag cctccaacac ccctccaga    2460 gcccgagacc tga                                                        2473

<210> SEQ ID NO 3
<211> LENGTH: 720
<212> TYPE: DNA
<213> ORGANISM: Aequorea victoria

<400> SEQUENCE: 3
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 4
<211> LENGTH: 136
<212> TYPE: DNA
<213> ORGANISM: Simian virus 40
```

<400> SEQUENCE: 4

```
aacttgttta ttgcagctta taatggttac aaataaagca atagcatcac aaatttcaca    60
aataaagcat ttttttcact gcattctagt tgtggtttgt ccaaactcat caatgtatct   120
tatcatgtct gtatcc                                                   136
```

<210> SEQ ID NO 5
<211> LENGTH: 58
<212> TYPE: DNA
<213> ORGANISM: artificial sequence
<220> FEATURE:
<223> OTHER INFORMATION: Synthetic poly A sequence utilized in cloning
      vectors

<400> SEQUENCE: 5

```
aataaaatat ctttattttc attacatctg tgtgttggtt ttttgtgtga atcgatag      58
```

<210> SEQ ID NO 6
<211> LENGTH: 1518
<212> TYPE: DNA
<213> ORGANISM: human papilloma virus

<400> SEQUENCE: 6

```
atgagcctgt ggctgcccag cgaggccacc gtgtacctgc ccccgtgcc cgtgagcaag     60
gtggtgagca ccgacgagta cgtggccagg accaacatct actaccacgc cggcaccagc   120
aggctgctgg ccgtgggcca cccctacttc cccatcaaga agcccaacaa caacaagatc   180
ctggtgccca aggtgagcgg cctgcagtac agggtgttca ggatccacct gcccgacccc   240
aacaagttcg gcttccccga caccagcttc tacaaccccg acacccagag gctggtgtgg   300
gcctgcgtgg gcgtggaggt gggcaggggc cagcccctgg gcgtgggcat cagcggccac   360
cccctgctga acaagctgga cgacaccgag aacgccagcg cctacgccgc caacgccggc   420
gtggacaaca gggagtgcat cagcatggac tacaagcaga cccagctgtg cctgatcggc   480
tgcaagcccc ccatcggcga gcactggggc aagggcagcc cctgcaccaa cgtggccgtg   540
aaccccggcg actgcccccc cctggagctg atcaacaccg tgatccagga cggcgacatg   600
gtggacaccg gcttcggcgc catggacttc accaccctgc aggccaacaa gagcgaggtg   660
cccctggaca tctgcaccag catctgcaag taccccgact acatcaagat ggtgagcgag   720
ccctacggcg acagcctgtt cttctacctg aggagggagc agatgttcgt gaggcacctg   780
ttcaacaggg ccggcgccgt gggcgagaac gtgcccgacg acctgtacat caagggcagc   840
ggcagcaccg ccaacctggc cagcagcaac tacttcccca ccccagcgg cagcatggtg   900
accagcgacg cccagatctt caacaagccc tactggctgc agagggccca gggccacaac   960
aacggcatct gctggggcaa ccagctgttc gtgaccgtgg tggacaccac caggagcacc  1020
aacatgagcc tgtgcgccgc catcagcacc agcgagacca cctacaagaa caccaacttc  1080
aaggagtacc tgaggcacgg cgaggagtac gacctgcagt tcatcttcca gctgtgcaag  1140
atcaccctga ccgccgacgt gatgacctac atccacagca tgaacagcac catcctggag  1200
gactggaact tcggcctgca gcccccccc ggcggcaccc tggaggacac ctacaggttc  1260
gtgaccagcc aggccatcgc ctgccagaag cacacccccc ccgccccaa ggaggacccc  1320
ctgaagaagt acaccttctg ggaggtgaac ctgaaggaga agttcagcgc cgacctggac  1380
```

-continued

| | |
|---|---|
| cagttccccc tgggcaggaa gttcctgctg caggccggcc tgaaggccaa gcccaagttc | 1440 |
| accctgggca agaggaaggc caccccacc accagcagca ccagcaccac cgccaagagg | 1500 |
| aagaagagga agctgtga | 1518 |

<210> SEQ ID NO 7
<211> LENGTH: 1422
<212> TYPE: DNA
<213> ORGANISM: Human papilloma virus

<400> SEQUENCE: 7

| | |
|---|---|
| atgaggcaca agaggagcgc caagaggacc aagagggcca gcgccaccca gctgtacaag | 60 |
| acctgcaagc aggccggcac ctgccccccc gacatcatcc caaggtgga gggcaagacc | 120 |
| atcgccgacc agatcctgca gtacggcagc atgggcgtgt tcttcggcgg cctgggcatc | 180 |
| ggcaccggca gcggcaccgg cggcaggacc ggctacatcc ccctgggcac caggcccccc | 240 |
| accgccaccg acaccctggc ccccgtgagg ccccccctga ccgtggaccc cgtgggcccc | 300 |
| agcgacccca gcatcgtgag cctggtggag gagaccagct tcatcgacgc cggcgccccc | 360 |
| accagcgtgc ccagcatccc ccccgacgtg agcggcttca gcatcaccac cagcaccgac | 420 |
| accaccccg ccatcctgga catcaacaac accgtgacca ccgtgaccac ccacaacaac | 480 |
| cccaccttca ccgaccccag cgtgctgcag cccccaccc cgccgagac cggcggccac | 540 |
| ttcaccctga gcagcagcac catcagcacc cacaactacg aggagatccc catggacacc | 600 |
| ttcatcgtga gcaccaaccc caacaccgtg accagcagca cccccatccc cggcagcagg | 660 |
| cccgtggcca ggctgggcct gtacagcagg accacccagc aggtgaaggt ggtggacccc | 720 |
| gccttcgtga ccaccccccac caagctgatc acctacgaca ccccgccta cgagggcatc | 780 |
| gacgtggaca acaccctgta cttcagcagc aacgacaaca gcatcaacat cgccccgac | 840 |
| cccgacttcc tggacatcgt ggccctgcac aggcccgccc tgaccagcag gaggaccggc | 900 |
| atcaggtaca gcaggatcgg caacaagcag accctgagga ccaggagcgg caagagcatc | 960 |
| ggcgccaagg tgcactacta ctacgacctg agcaccatcg accccgccga ggagatcgag | 1020 |
| ctgcagacca tcaccccccag cacctacacc accaccagcc acgccgccag ccccaccagc | 1080 |
| atcaacaacg gcctgtacga catctacgcc gacgacttca tcaccgacac cagcaccacc | 1140 |
| cccgtgccca cgtgcccag caccagcctg agcggctaca tccccgccaa caccaccatc | 1200 |
| cccttcggtg gcgcctacaa catccccctg gtgagcggcc ccgacatccc catcaacatc | 1260 |
| accgaccagg ccccagcct gatccccatc gtgcccggca gccccagta ccatcatc | 1320 |
| gccgacgccg gcgacttcta cctgcacccc agctactaca tgctgaggaa gaggaggaag | 1380 |
| aggctgccct acttcttcag cgacgtgagc ctggccgcct ga | 1422 |

<210> SEQ ID NO 8
<211> LENGTH: 1488
<212> TYPE: DNA
<213> ORGANISM: Bovine papilloma virus

<400> SEQUENCE: 8

| | |
|---|---|
| atggctctgt ggcagcaggg gcagaaactg tatctgcctc caactcccgt gtcaaaagtc | 60 |
| ctgtgctccg aaacctatgt ccagcgaaag tccatctttt accacgccga gacagagagg | 120 |
| ctgctgacaa tcggccaccc atactatccc gtgtccatcg cgccaagac agtgcccaag | 180 |
| gtgtctgcca accagtatcg cgtgtttaag atccagctgc ccgaccctaa ccagttcgcc | 240 |

-continued

```
ctgcctgata ggaccgtgca caatccaagc aaggagcgcc tggtgtgggc cgtgatcgga      300
gtgcaggtgt ccaggggaca gccactggga ggcaccgtga caggccaccc taccttcaat      360
gccctgctgg acgccgagaa cgtgaatagg aaggtgacca cacagaccac agacgatcgc      420
aagcagaccg gcctggatgc caagcagcag cagatcctgc tgctgggatg cacaccagca      480
gagggcgagt actggaccac agccaggccc tgcgtgaccg acaggctgga gaatggagca      540
tgtccacctc tggagctgaa gaataagcac atcgaggacg gcgatatgat ggagatcggc      600
tttggcgccg ccaacttcaa ggagatcaat gccagcaagt ccgacctgcc tctggacatc      660
cagaacgaga tctgtctgta cccagactat ctgaagatgg ccgaggatgc cgccggcaat      720
tccatgttct ttttcgccag aaaggagcag gtgtacgtgc ggcacatctg gaccagagga      780
ggaagcgaga aggaggcacc taccacagac ttttatctga agaacaataa gggcgatgcc      840
acactgaaga tcccctctgt gcacttcggc tctcctagcg gctccctggt gagcaccgac      900
aaccagatct ttaatcggcc atactggctg ttcagagccc agggcatgaa caatggcatc      960
gcctggaaca atctgctgtt cctgaccgtg ggcgataaca cccggggcac aaatctgacc     1020
atctctgtgg caagcgacgg aacaccactg accgagtatg atagctccaa gtttaacgtg     1080
taccacagac acatggagga gtataagctg gccttcatcc tggagctgtg ctccgtggag     1140
atcacagccc agaccgtgtc tcacctgcag ggcctgatgc ccagcgtgct ggagaattgg     1200
gagatcggcg tgcagccacc cacctctagc atcctggagg acacatacag gtatatcgag     1260
agccctgcca ccaagtgcgc ctccaacgtg atccccgcca aggaggaccc ttacgccggc     1320
tttaagttct ggaatatcga tctgaaggag aagctgagcc tggacctgga tcagtttcca     1380
ctgggccgga gattcctggc acagcaggga gcaggatgtt ccaccgtgcg caagaggcgc     1440
atctctcaga agacatcctc taagcccgcc aagaagaaga agaagtga                  1488
```

<210> SEQ ID NO 9
<211> LENGTH: 1410
<212> TYPE: DNA
<213> ORGANISM: Bovine papilloma virus

<400> SEQUENCE: 9

```
atgagcgcca ggaagagggt gaagagggca tccgcctacg acctgtatag aacctgcaag      60
caggccggca catgtcctcc agatgtgatc cccaaggtgg agggcgacac catcgccgat     120
aagatcctga gtttggagg cctggcaatc tacctgggag gctgggaat cggaacatgg     180 tctaccggaa gggtggcagc aggaggcagc ccaaggtata caccactgag gaccgcagga     240
tctacaagct ccctggcatc catcggctct agggcagtga cagcaggaac ccgcccaagc     300
atcggagcag gaatcccact ggacacactg gagacactgg gcgccctgcg gcccggcgtg     360
tacgaggaca ccgtgctgcc tgaggcacca gccatcgtga cacctgatgc agtgccagca     420
gactctggcc tggatgcact gagcatcggc accgattcta gcaccgagac actgatcaca     480
ctgctggagc cagagggacc tgaggacatc gccgtgctgg agctgcagcc actggatcgg     540
cctacatggc aggtgagcaa cgccgtgcac cagtcctctg cctaccacgc ccctctgcag     600
ctgcagagct ccatcgccga caagcggcct ggagaacaa tctttgtggg aggctccggc     660
ctgggcgaca ccggaggcga gaatatcgag ctgacatatt tcggcagccc acggacctcc     720
acacccagat ctatcgcctc taagagccgg ggcatcctga actggttctc caagagatac     780 tatcccagg tgccaacaga ggaccccgag gtgtttttcta gccagacctt cgccaatcct     840
ctgtacgagg cagagccagc cgtgctgaag ggaccatccg gaagagtggg cctgtctcag      900
```

```
gtgtataagc cagataccct gaccacacgg agcggaacag aagtgggacc acagctgcac    960
gtgagatact ccctgtctac catccacgag gacgtggagg ccatccctta taccgtggat   1020
gagaacacac agggcctggc ctttgtgcca ctgcacgagg agcaggccgg ctttgaggag   1080
atcgagctgg acgatttctc cgagacacac aggctgctgc ctcagaatac atcctctacc   1140
ccagtgggaa gcggcgtgcg gagatccctg atcccaaccc aggagttctc cgccacacgc   1200
cccaccggag tggtgaccta cggctctcct gatacatata gcgcctcccc tgtgaccgac   1260
ccagattcta caagcccctc cctggtcatc gacgatacca aaccacacc tatcatcatc    1320 atcgacggcc acaccgtgga tctgtacagc tcaaactaca ccctgcaccc atccctgctg   1380
cggaagagaa agaaacggaa acacgcctaa                                    1410

<210> SEQ ID NO 10
<211> LENGTH: 705
<212> TYPE: DNA
<213> ORGANISM: Oplophorus gracilirostris

<400> SEQUENCE: 10
atgaactcct tctcaacttc cgcctttgga cccgtcgcat tttctctggg gctgctgctg     60
gtgctgcctg ccgcctttcc tgctcccgtg ttcacactgg aggactttgt gggcgattgg    120
aggcagaccg ccggctacaa cctggaccag gtgctggagc agggaggcgt gagctccctg    180
ttccagaatc tgggcgtgag cgtgacaccc atccagagga tcgtgctgtc cggcgagaac    240
ggcctgaaga tcgacatcca cgtgatcatc ccttatgagg gcctgtctgg cgatcagatg    300
ggccagatcg agaagatctt caaggtggtg tacccagtgg acgatcacca cttcaaagtg    360
atcctgcact atggcaccct ggtcatcgac ggcgtgaccc caaatatgat cgattacttc    420
ggcagaccct atgagggcat cgccgtgttc gatggcaaga gatcaccgt gacaggcacc     480 ctgtggaacg gcaataagat catcgacgag cggctgatca accccgatgg cagcctgctg    540
tttagggtga caatcaatgg agtgaccgga tggaggctgt gcgagagaat cctggctctc    600
gagaccggtg gcggtggcgg tggtggcggt ggctctgact acaaagacga tgacgataaa    660
gggggcggtg gaggttaccc atacgatgtt ccagattacg cttaa                    705

<210> SEQ ID NO 11
<211> LENGTH: 5726
<212> TYPE: DNA
<213> ORGANISM: artificial sequence
<220> FEATURE:
<223> OTHER INFORMATION: Control plasmid construct pcDNA-GFP

<400> SEQUENCE: 11
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
```

-continued

| | |
|---|---|
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttcgaa ttctgcagtc gacggtaccg cgggcccggg atccaccggt | 960 |
| cgccaccatg gtgagcaagg gcgaggagct gttcaccggg gtggtgccca tcctggtcga | 1020 |
| gctggacggc gacgtaaacg gccacaagtt cagcgtgtcc ggcgagggcg agggcgatgc | 1080 |
| cacctacggc aagctgaccc tgaagttcat ctgcaccacc ggcaagctgc ccgtgccctg | 1140 |
| gcccaccctc gtgaccaccc tgacctacgg cgtgcagtgc ttcagccgct accccgacca | 1200 |
| catgaagcag cacgacttct tcaagtccgc catgcccgaa ggctacgtcc aggagcgcac | 1260 |
| catcttcttc aaggacgacg gcaactacaa gacccgcgcc gaggtgaagt tcgagggcga | 1320 |
| caccctggtg aaccgcatcg agctgaaggg catcgacttc aaggaggacg gcaacatcct | 1380 |
| ggggcacaag ctggagtaca actacaacag ccacaacgtc tatatcatgg ccgacaagca | 1440 |
| gaagaacggc atcaaggtga acttcaagat ccgccacaac atcgaggacg gcagcgtgca | 1500 |
| gctcgccgac cactaccagc agaacacccc catcggcgac ggccccgtgc tgctgcccga | 1560 |
| caaccactac ctgagcaccc agtccgccct gagcaaagac cccaacgaga gcgcgatca | 1620 |
| catggtcctg ctggagttcg tgaccgccgc cgggatcact ctcggcatgg acgagctgta | 1680 |
| caagtaaagc ggccgctcga gtctagaggg cccgtttaaa cccgctgatc agcctcgact | 1740 |
| gtgccttcta gttgccagcc atctgttgtt tgccccctcc ccgtgccttc cttgaccctg | 1800 |
| gaaggtgcca ctcccactgt cctttcctaa taaaatgagg aaattgcatc gcattgtctg | 1860 |
| agtaggtgtc attctattct ggggggtggg gtggggcagg acagcaaggg ggaggattgg | 1920 |
| gaagacaata gcaggcatgc tggggatgcg gtgggctcta tggcttctga ggcggaaaga | 1980 |
| accagctggg gctctagggg gtatccccac gcgccctgta gcggcgcatt aagcgcggcg | 2040 |
| ggtgtggtgg ttacgcgcag cgtgaccgct acacttgcca gcgccctagc gcccgctcct | 2100 |
| ttcgctttct tcccttcctt tctcgccacg ttcgccggct ttccccgtca gctctaaat | 2160 |
| cggggcatcc ctttagggtt ccgatttagt gctttacggc acctcgaccc caaaaaactt | 2220 |
| gattagggtg atggttcacg tagtgggcca tcgccctgat agacggtttt tcgcccttttg | 2280 |
| acgttggagt ccacgttctt taatagtgga ctcttgttcc aaactggaac aacactcaac | 2340 |
| cctatctcgg tctattcttt tgatttataa gggattttgg ggatttcggc ctattggtta | 2400 |
| aaaaatgagc tgatttaaca aaaatttaac gcgaattaat tctgtggaat gtgtgtcagt | 2460 |
| tagggtgtgg aaagtcccca ggctccccag gcaggcagaa gtatgcaaag catgcatctc | 2520 |
| aattagtcag caaccaggtg tggaaagtcc ccaggctccc cagcaggcag aagtatgcaa | 2580 |
| agcatgcatc tcaattagtc agcaaccata gtcccgcccc taactccgcc catcccgccc | 2640 |
| ctaactccgc ccagttccgc ccattctccg ccccatggct gactaatttt ttttatttat | 2700 |
| gcagaggccg aggccgcctc tgcctctgag ctattccaga agtagtgagg aggcttttt | 2760 |
| ggaggcctag gcttttgcaa aaagctcccg ggagcttgta tatccatttt cggatctgat | 2820 |
| cagcacgtgt tgacaattaa tcatcggcat agtatatcgg catagtataa tacgacaagg | 2880 |
| tgaggaacta aaccatggcc aagttgacca gtgccgttcc ggtgctcacc gcgcgcgacg | 2940 |

```
tcgccggagc ggtcgagttc tggaccgacc ggctcgggtt ctcccgggac ttcgtggagg   3000
acgacttcgc cggtgtggtc cgggacgacg tgaccctgtt catcagcgcg gtccaggacc   3060
aggtggtgcc ggacaacacc ctggcctggg tgtgggtgcg cggcctggac gagctgtacg   3120
ccgagtggtc ggaggtcgtg tccacgaact tccgggacgc ctcccgggcc gccatgaccg   3180
agatcggcga gcagccgtgg gggcgggagt tcgccctgcg cgacccggcc ggcaactgcg   3240
tgcacttcgt ggccgaggag caggactgac acgtgctacg agatttcgat tccaccgccg   3300
ccttctatga aaggttgggc ttcggaatcg ttttccggga cgccggctgg atgatcctcc   3360
agcgcgggga tctcatgctg gagttcttcg cccaccccaa cttgtttatt gcagcttata   3420
atggttacaa ataaagcaat agcatcacaa atttcacaaa taaagcattt ttttcactgc   3480
attctagttg tggtttgtcc aaactcatca atgtatctta tcatgtctgt ataccgtcga   3540
cctctagcta gagcttggcg taatcatggt catagctgtt tcctgtgtga aattgttatc   3600
cgctcacaat tccacacaac atacgagccg gaagcataaa gtgtaaagcc tggggtgcct   3660
aatgagtgag ctaactcaca ttaattgcgt tgcgctcact gcccgctttc cagtcgggaa   3720
acctgtcgtg ccagctgcat taatgaatcg gccaacgcgc ggggagaggc ggtttgcgta   3780
ttgggcgctc ttccgcttcc tcgctcactg actcgctgcg ctcggtcgtt cggctgcggc   3840
gagcggtatc agctcactca aaggcggtaa tacggttatc cacagaatca ggggataacg   3900
caggaaagaa catgtgagca aaaggccagc aaaaggccag gaaccgtaaa aaggccgcgt   3960
tgctggcgtt tttccatagg ctccgccccc ctgacgagca tcacaaaaat cgacgctcaa   4020
gtcagaggtg gcgaaacccg acaggactat aaagatacca ggcgtttccc cctggaagct   4080
ccctcgtgcg ctctcctgtt ccgaccctgc cgcttaccgg atacctgtcc gcctttctcc   4140
cttcgggaag cgtggcgctt tctcaatgct cacgctgtag gtatctcagt tcggtgtagg   4200
tcgttcgctc caagctgggc tgtgtgcacg aaccccccgt tcagcccgac cgctgcgcct   4260
tatccggtaa ctatcgtctt gagtccaacc cggtaagaca cgacttatcg ccactggcag   4320
cagccactgg taacaggatt agcagagcga ggtatgtagg cggtgctaca gagttcttga   4380
agtggtggcc taactacggc tacactagaa ggacagtatt tggtatctgc gctctgctga   4440
agccagttac cttcggaaaa agagttggta gctcttgatc cggcaaacaa accaccgctg   4500
gtagcggtgg ttttttttgtt tgcaagcagc agattacgcg cagaaaaaaa ggatctcaag   4560
aagatccttt gatcttttct acggggtctg acgctcagtg gaacgaaaac tcacgttaag   4620
ggattttggt catgagatta tcaaaaagga tcttcaccta gatcctttta aattaaaaat   4680
gaagttttaa atcaatctaa agtatatatg agtaaacttg gtctgacagt taccaatgct   4740
taatcagtga ggcacctatc tcagcgatct gtctatttcg ttcatccata gttgcctgac   4800
tccccgtcgt gtagataact acgatacggg agggcttacc atctggcccc agtgctgcaa   4860
tgataccgcg agacccacgc tcaccggctc cagatttatc agcaataaac cagccagccg   4920
gaagggccga gcgcagaagt ggtcctgcaa ctttatccgc ctccatccag tctattaatt   4980
gttgccggga agctagagta agtagttcgc cagttaatag tttgcgcaac gttgttgcca   5040
ttgctacagg catcgtggtg tcacgctcgt cgtttggtat ggcttcattc agctccggtt   5100
cccaacgatc aaggcgagtt acatgatccc ccatgttgtg caaaaaagcg gttagctcct   5160
tcggtcctcc gatcgttgtc agaagtaagt tggccgcagt gttatcactc atggttatgg   5220
cagcactgca taattctctt actgtcatgc catccgtaag atgcttttct gtgactggtg   5280
```

```
agtactcaac caagtcattc tgagaatagt gtatgcggcg accgagttgc tcttgcccgg    5340
cgtcaatacg gataatacc gcgccacata gcagaacttt aaaagtgctc atcattggaa    5400
aacgttcttc ggggcgaaaa ctctcaagga tcttaccgct gttgagatcc agttcgatgt    5460
aacccactcg tgcacccaac tgatcttcag catcttttac tttcaccagc gtttctgggt    5520
gagcaaaaac aggaaggcaa aatgccgcaa aaagggaat aagggcgaca cggaaatgtt     5580
gaatactcat actcttcctt tttcaatatt attgaagcat ttatcagggt tattgtctca    5640
tgagcggata catatttgaa tgtatttaga aaaataaaca aatagggtt ccgcgcacat     5700 ttccccgaaa agtgccacct gacgtc                                         5726

<210> SEQ ID NO 12
<211> LENGTH: 72
<212> TYPE: DNA
<213> ORGANISM: simian virus 40

<400> SEQUENCE: 12
tggttgctga ctaattgaga tgcatgcttt gcatacttct gcctgctggg gagcctgggg    60
actttccaca cc                                                        72

<210> SEQ ID NO 13
<211> LENGTH: 288
<212> TYPE: DNA
<213> ORGANISM: simian virus 40

<400> SEQUENCE: 13
tggttgctga ctaattgaga tgcatgcttt gcatacttct gcctgctggg gagcctgggg    60
actttccaca cctggttgct gactaattga gatgcatgct tgcatactt ctgcctgctg    120 gggagcctgg gactttcca cacctggttg ctgactaatt gagatgcatg ctttgcatac    180
ttctgcctgc tggggagcct ggggactttc cacacctggt tgctgactaa ttgagatgca    240
tgctttgcat acttctgcct gctggggagc ctggggactt ccacacc                  288
```

PROBE FOR UNIVERSAL DETECTION OF CIRCULATING TUMOR CELLS

REFERENCE TO RELATED APPLICATIONS

This application claims priority based on U.S. Provisional Application Ser. No. 62/630,570 filed Feb. 14, 2018, incorporated herein by reference in its entirety.

STATEMENT OF GOVERNMENT INTEREST

This invention was made with government support under 1 R01 CA187923-01A1 and 1 R01 CA203852-01 awarded by the National Cancer Institute of the National Institutes of Health. The government has certain rights in the invention.

FIELD OF THE INVENTION

The present invention is directed to probes that can be used for detecting circulating tumor cells (CTCs) in the blood stream, and methods for using such probes to detect CTCs.

BACKGROUND OF THE INVENTION

Circulating tumor cells (CTCs) are malignant cells that have entered into the blood stream from either the primary tumor or metastatic sites. It is believed that CTCs appear in the circulating blood at a relatively early stage of tumor growth. As CTCs can be easily accessed through liquid biopsy, they are an attractive source for various applications in oncology, including the possibility for early diagnosis, evaluation of chemotherapeutic efficacy and cancer prognosis, and choice of individual-specific anti-cancer drugs. However, despite intensive recent research, there is still a lack of effective and simple methods for isolation and/or detection of CTCs in the blood, leading to poor prognoses. This is particularly true for visceral tumors such as pancreatic and lung cancers, which may not produce clear and unique clinical symptoms until a relatively late stage. Several reasons have contributed to the lack of efficient methods for detecting CTCs. First, CTCs are only a tiny fraction of the total amount of blood cells. Second, CTCs, like the tumor cells they originate from, lack unique, well-defined universal surface markers amongst all malignant cell types. Third, it is believed that many CTCs undergo epithelial to mesenchymal transition (EMT), which may result in change of surface markers associated with malignancy.

Currently, there are two major categories of isolation/identification strategies for CTCs: 1) immuno-based capture/depletion that relies on immunological recognition of unique biomarkers (i.e. EpCAM) and 2) techniques that exploit physical properties of the CTCs. Each strategy has its own shortcomings.

With respect to the first detection method, immuno-based capture/deletion, CELLSEARCH™ is an example of an immuno-based capture approach and is the only one that has received FDA approval for CTC detection. It enriches for CTCs in whole blood by first binding them through an anti-EpCAM-antibody conjugated to iron nanoparticles, followed by magnetic capture. CTCs are then further characterized and confirmed by: 1) DAPI staining to identify nucleated cells, 2) more antibody staining for epithelial structural cytokeratins (CK8, CK18, and CK19), and 3) anti-CD45 to differentiate CTCs from circulating white blood cells (WBCs). It is a cumbersome and costly detection method. More importantly, it may only be able to capture a relatively small fraction of the CTCs in the blood, mainly due to the heterogeneous nature of tumor cells and the biomarkers it relies on for detection.

With respect to the second detection method, exploiting CTC physical properties, isolating CTCs based on physical properties mainly relies on the relatively large size of CTCs. Several methods based on this principle have been reported. They include using a filter-based membrane with a specific pore size, microfluidic devices depending on both the size and the ability of the CTCs to deform in their enrichment strategies, and devices combining density centrifugation with size-based filtration. One of the main drawbacks for the physical property-based isolation is that many blood cells such as monocytes/macrophages are similar in size or even larger than CTCs, and as such, are not separated from the CTCs after the isolation procedure. As such, CTCs isolated from physical property-based methods frequently need to be further confirmed by either immune-staining or RT-PCR analysis, which is cumbersome and costly.

Thus, there is need in the art for effective and simple devices and methods for isolation and/or detection of CTCs in the blood.

SUMMARY OF THE INVENTION

A summary of certain embodiments disclosed herein is set forth below. It's understood that this section is presented merely to provide the reader with a brief summary of certain embodiments and that these descriptions are not intended to limit this application's scope. Indeed, this disclosure may encompass a variety of embodiments that may not be set forth herein.

Disclosed herein are probes for detecting circulating tumor cells (CTCs) in the blood, including methods of manufacturing such probes, and methods for using such probes to detect CTCs. In an embodiment, the probe can include a modified SV40 virus packaged into a capsid formed from L1 and L2 capsid proteins of human or bovine or other papillomavirus. The probe can include a marker gene, which can include green fluorescent protein gene (GFP), the luciferase gene (Luc), β-galactosidase, chloroamphenicol acetyltransferase (CAT) enzyme, and a membrane protein containing a tag. In an embodiment, the SV40 virus can be modified in at least three ways, including by eliminating the endogenous start codon, by inserting four 72 base pair (bp) tandem repeat enhancer sequences, and/or by substituting nucleotide 298 from cytosine (C) to thymine (T), nucleotide 299 from cytosine to thymine, nucleotide 304 from cytosine to thymine, and/or nucleotide 322 from G to C in wild type SV40.

In an embodiment, the probes disclosed herein are made by co-transfecting papilloma virus L1 and L2 genes with a modified SV40 construct into mammalian cells, or by in vitro assembly of the modified SV40 construct into capsids formed from co-transfecting the papilloma virus L1 and L2 genes into mammalian cells.

In another embodiment, the probes disclosed herein are used to detect CTCs in the blood. Blood is collected from a patient and nucleated cells are isolated from the blood, such as PBMCs and CTCs. A mixture can be prepared that includes the isolated nucleated cells the probes disclosed herein. Once mixed, the CTCs can be detected in the mixture.

BRIEF DESCRIPTION OF THE DRAWINGS

The foregoing summary, as well as the following detailed description, will be better understood when read in conjunction with the appended drawings and sequence listing. For the purpose of illustration only, there is shown in the drawings certain embodiments. It is understood, however, that the inventive concepts disclosed herein are not limited to the precise arrangements and instrumentalities shown in the figures.

DETAILED DESCRIPTION OF THE INVENTION

Figure 1A:
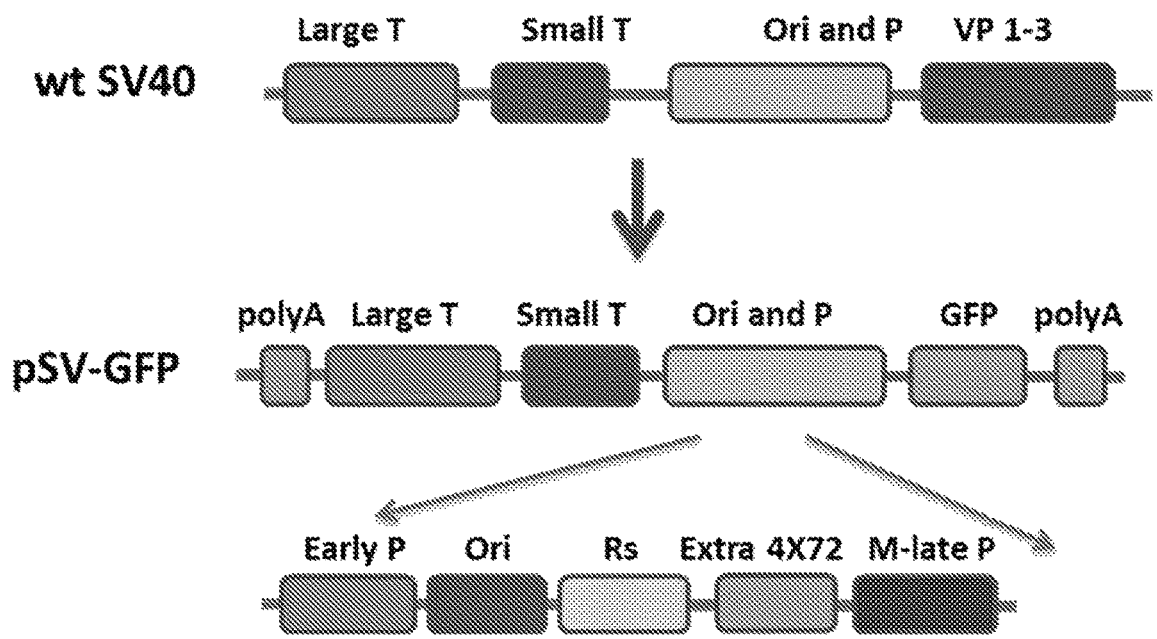
FIG. 1A illustrates the detailed components of the SV40 probe (pSV-GFP) and the introduced modifications for its construction, in accordance with embodiments disclosed herein and the sequence information from SEQ ID NOs: 1-5. The Simian Virus 40 (SV40) genome sequence used for modification comes from 776 wild strain (GenBank: J02400.1). The Large T and Small T sequence were optimized for human expression when they were synthesized. Several changes were introduced into the SV40 genome, including: 1) insertion of an extra 4×72 base pair (bp) tandem repeat enhancer sequences (SEQ ID NO: 13), 2) nucleotide mutations at number 671, 672 and 677 from C to T of SEQ ID NO: 1, at number 695 G to C of SEQ ID NO: 1, and 3) the nucleotide sequence at number 708 of SEQ ID NO: 1 is mutated from A to C to delete the original start codon. The GFP gene in the pSV-GFP could be other marker genes such as luciferase. In an embodiment, the luciferase gene can be SEQ ID NO: 10, which is from the Deep Sea Shrimp and is termed "Sluc" (secreted nano-luciferase), modified by humanization and by linking it with Flag and HA tags. The advantages of selecting Sluc are: 1) its sequence is much shorter than those commonly used luciferase genes such as Firefly and Renilla Luc genes, which is important as VLPs from papilloma viruses have limited packaging capacity, 2) it is significantly more stable than other luciferase so that it can accumulate for easy detection, and 3) it is naturally secreted and this makes the detection easier.

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented systems, methods, features, and advantages will be or become apparent to one with skill in the art upon examining the drawings and the detailed description herein. It is intended that all such additional systems, methods, features, and advantages be protected by the accompanying claims.

Disclosed herein is a novel universal probe that can be used in a simple procedure to accurately detect CTCs in the blood with extremely high sensitivity. As used herein the term "CTC-UniPro" stands for "CTC universal probe" and is a novel probe containing two key components. The first component, a virus-like particle (VLP) formed from the L1 and L2 proteins of human papillomavirus (HPV) and/or bovine papilloma virus (BPV) or papilloma virus from other species, enables the probe to selectively enter CTCs, but not other blood cells. This provides the probe with an extremely high degree of specificity for detecting CTCs in the blood stream. The second component, a modified SV-40 virus genome disclosed herein that contains a marker gene and is packaged into the VLP, enables the probe to extensively amplify within the tumor cells. This provides the probe with a high sensitivity for detecting CTCs that are rarely presented and at a low concentration in the blood. A major issue with entirely SV40 based probes is that they can enter other blood cells, such as T cells and monocytes, in addition to CTCs. Replacing the SV40 capsid with the VLP formed from HPV or other papilloma viruses exploits the fact that the majority of cancer cells are of epithelial origin and papilloma viruses exclusively infect epithelial cells. Thus, this novel probe combines the specificity of the HPV-VLP mediated entry and the sensitivity provided by the SV40 amplification.

When mononuclear cells prepared from healthy donors are mixed with a CTC-UniPro carrying the green fluorescent protein (GFP) marker gene, not a single GFP positive cell is detected. When the same mononuclear cells prepared from healthy donors are mixed with a CTC-UniPro carrying the luciferase marker gene, only a very low background signal was detected with sensitive machines. These prove the extreme specificity of the probe as it does not detect any normal blood cells. However, when the same mononuclear cells spiked with tumor cells are mixed with this CTC- UniPro, the tumor cells are detected with high accuracy and sensitivity. The same experiment can be repeated with almost a dozen tumor cells of different tissue origin, and in each case the spiked tumor cells are readily detected with the CTC-UniPro. This proves that the probe can be universally used to detect virtually any type of tumor. CTC-UniPro carrying a tagged membrane protein allows CTCs to be precisely collected for further analysis.

The CTC-UniPro is a specific and sensitive probe for reliably detecting CTCs with simplicity, which may lead to earlier diagnoses of a wide range of cancer types, better evaluation of chemotherapeutic efficacy and cancer prognosis, and better selection of individual-specific anti-cancer drugs.

In one embodiment, the CTC-UniPro is based on a modified SV40 virus, which can undergo enormous amplification within a short period of time, allowing for high sensitivity in detection.

In one embodiment, the SV40 virus can be modified by replacing the original capsid with a virus-like particle to increase the selectivity of the probe. For example, the capsid can be formed by the L1 and L2 capsid proteins of the human papillomavirus 16.

In an embodiment, the probe can be prepared by modification of SV40 virus so that it carries marker genes for easiness in detection. By way of example only, the marker genes can be the green fluorescent protein gene (GFP), the luciferase gene (Luc), β-galactosidase, chloroamphenicol acetyltransferase (CAT) enzyme, or a membrane protein containing a tag, such as HA tag. The marker gene is inserted downstream of the SV40 late promoter so that the marker will amplify with the virus, making the virus detectable. The late promoter of the SV40 gene can also be modified, increasing amplification of the marker gene. For example, interference from the SV40 endogenous start codon can be eliminated by substituting nucleotide 335 of adenine (A) with cytosine (C) in the wild type SV40 (shown as 708 from A to C in SEQ ID NO. 1), facilitating expression of the marker gene. In yet another embodiment, the 72 base pair enhancer sequence (252-323 of SEQ ID NO:1) which is further set out in SEQ ID NO: 12 is repeated four additional times (SEQ ID NO:13) and inserted as a 288 bp enhancer to strengthen the activity of the late promoter. Further, a series of nucleotide substitutions in the wild type SV40, 298 of cytosine (C) to thymine (T), 299 from C to T, and 304 from C to T (shown as 671, 672 and 677 from C to T of SEQ ID NO: 1), can also strengthen the late promoter's activity. Additional modification can include a nucleotide mutations at number 322 G to C in the wild type SV40 (shown as 695 from G to C in SEQ ID NO: 1). All these modifications are important for enabling the extremely high detection sensitivity of CTC-UniPro.

Figure 1B:
FIG. 1B illustrates the HPV16 L1 and L2 capsid for packaging the probe, in accordance with embodiments disclosed herein and the detailed sequence information from the SEQ ID NOs: 6-7. The same modified SV40 probe could also be packaged inside the capsid derived from L1 and L2 proteins from bovine papilloma virus (BPV) with the same efficiency, with the detailed sequence information from the SEQ ID NOs: 8-9.
Figure 1C:
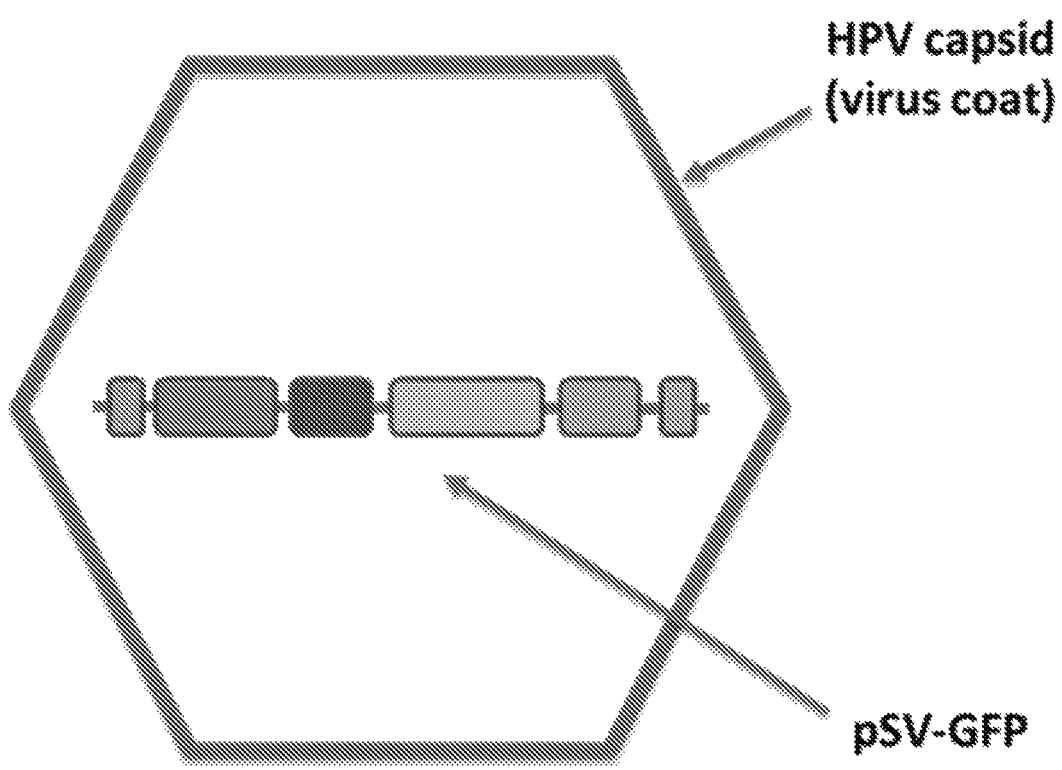
FIG. 1C illustrates the CTC-UniPro in the assembled form, with the pSV-GFP (the SV40 probe) packaged inside the capsid derived from HPV L1 and L2 proteins.

By way of example only, FIG. 1A-FIG. 1C illustrate construction of the CTC-UniPro probe described herein. The CTC-UniPro (FIG. 1C) can be formed by co-transfecting pSV-GFP (FIG. 1A) and pHPVL1,2 (FIG. 1B) into 293TT cells, which express high levels of large T and small T antigens of SV40.[14] Other mammalian cells can also be used albeit with a bit lower production efficiency. The pSV-GFP is packaged inside the capsid derived from HPV. After 48 to 72 hours, the cells can be collected and lysed with lyse buffer or through sonication. The probe can be collected by harvesting the supernatant after spinning down the cell debris. In another embodiment, the probe can be further purified by being passed through a GE Capto Core 700 column and then through a PD-10 column or by other purification procedures.

In yet another embodiment, the titer of the probe can be titrated by incubating the serial dilutions of the harvested probe with 293TT cells, and GFP positive cells can be quantitated by flow cytometry.

CTC-UniPro probes can also be assembled in vitro by mixing either purified L1 or by mixing VLP harvested from 293TT cells transfected with L1 and L2 with the pSV-GFP construct.

CTC-UniPro—Selective Detection of Tumor Cells from Healthy Cells

Figure 3A:
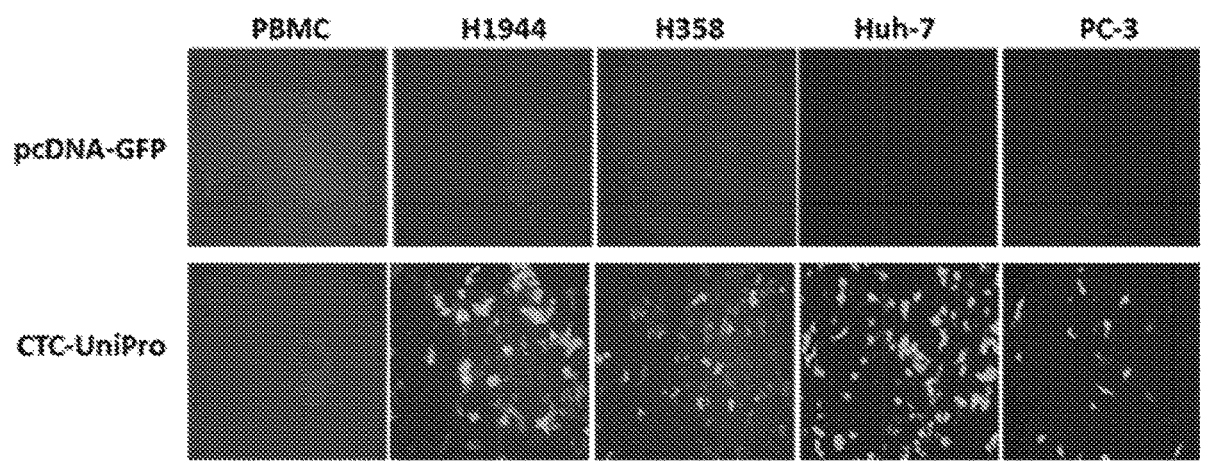
FIG. 3A illustrates the specific detection of malignant cells by CTC-UniPro but not by the control pcDNA-GFP construct, in accordance with embodiments disclosed herein.

In one embodiment, the CTC-UniPro described herein detects only tumor cells. For example, tumor cells from two different human lung cancer cell lines and peripheral blood mononuclear cells (PBMCs) from healthy blood can be mixed and incubated with equal amounts of CTC-UniPro for 24 to 72 hours. As shown in FIG. 3A, photos taken under a fluorescent microscope indicate that GFP positive cells are widely detected in the lung cancer cell lines, and that no GFP positive cells are detected in the PBMCs. In embodiments using tumor cells from 28 tumor cells lines (identified in the below Table 1) and PBMCs from three different donors, the CTC-UniPro achieved similar outcomes.

TABLE 1

Tumor Cell Lines

| Origin | Cell line | Origin | Cell line |
| --- | --- | --- | --- |
| Oral | SCC 25 | Kidney | ACHN |
| Head and neck | 22A H&N | Bladder | 5637 |
| Breast | MCF-7 | | T24 |
| | T47 | Cervix | Hela |
| | | Ovary | SKOV-3 |
| | MDA-MB-231 | | Hey |
| Lung | A549 | Prostate | DU145 |
| | H522 | | PC3 |
| | H358 | | |
| | H1944 | Skin | A-375 |
| | 5838 | | Mel 526 |
| Liver | Hep3B | | |
| | HUH-7 | | |
| Pancreas | Mpanc 96 | | |
| | Panc-1 | | |
| | BXpc3 | | |
| Colon | SW480 | | |
| | HCT-116 | | |
| | SW403 | | |

Figure 2A:
FIG. 2A illustrates the pcDNA-GFP control construct (SEQ ID NO: 11), in accordance with embodiments disclosed herein and the detailed sequence information from the sequence information from the SEQ ID NO: 11.
Figure 2B:
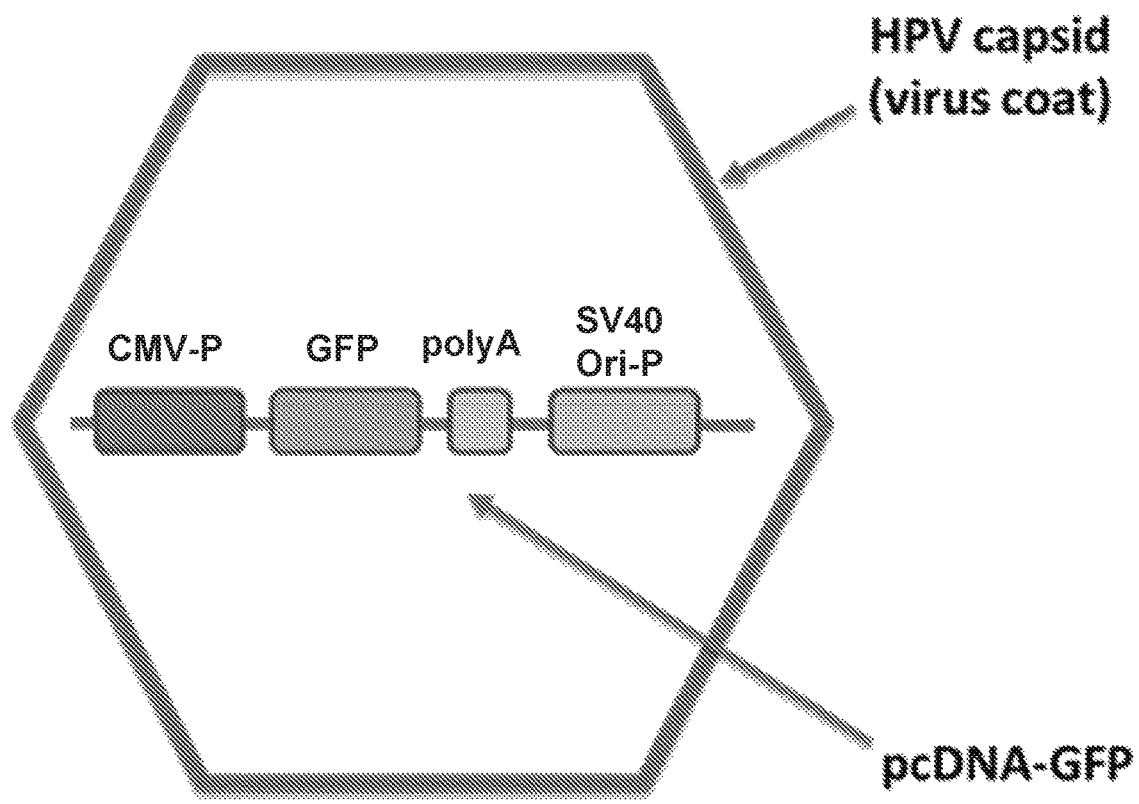
FIG. 2B illustrates the control pcDNA-GFP in the assembled form, with the control pcDNA-GFP packaged inside the capsid derived from HPV.

CTC-UniPro—Self-Amplification in Tumor Cells as a Result of the presence of T Antigens in the probe In an embodiment, the CTC-UniPro described herein is capable of self-amplifying in a wide variety of malignant cells. For example, in an embodiment, a control construct can be packaged into the same HPV capsid shell as the CTC-UniPro. As illustrated in FIGS. 2A-2B, this control can include a pcDNA-GFP control construct (FIG. 2A) containing a GFP driven by a potent mammalian promoter, the cytomegalovirus immediate early promoter (CMV-P), and the SV40 replication origin (Ori) and promoters. The control construct (FIG. 2B) can be formed by co-transfecting pcDNA-GFP control construct (FIG. 2A) and pHPVL1,2 (FIG. 1B) into 293TT cells. The pcDNA-GFP control construct is packaged inside the capsid derived from HPV. The pcDNA-GFP alone lacks the T antigens contained in CTC-UniPro, which are necessary for self-amplification.[15]

Figure 3B:
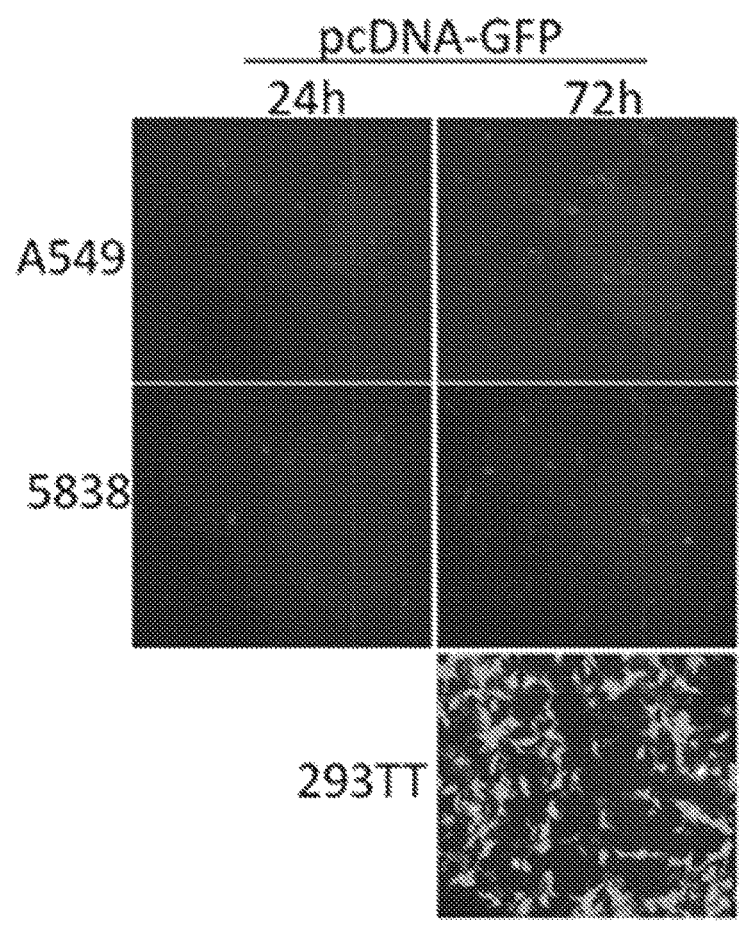
FIG. 3B illustrates detection of human lung cancer cell lines (A549 and 5838) by the pcDNA-GFP control construct, in accordance with embodiments disclosed herein.
Figure 3C:
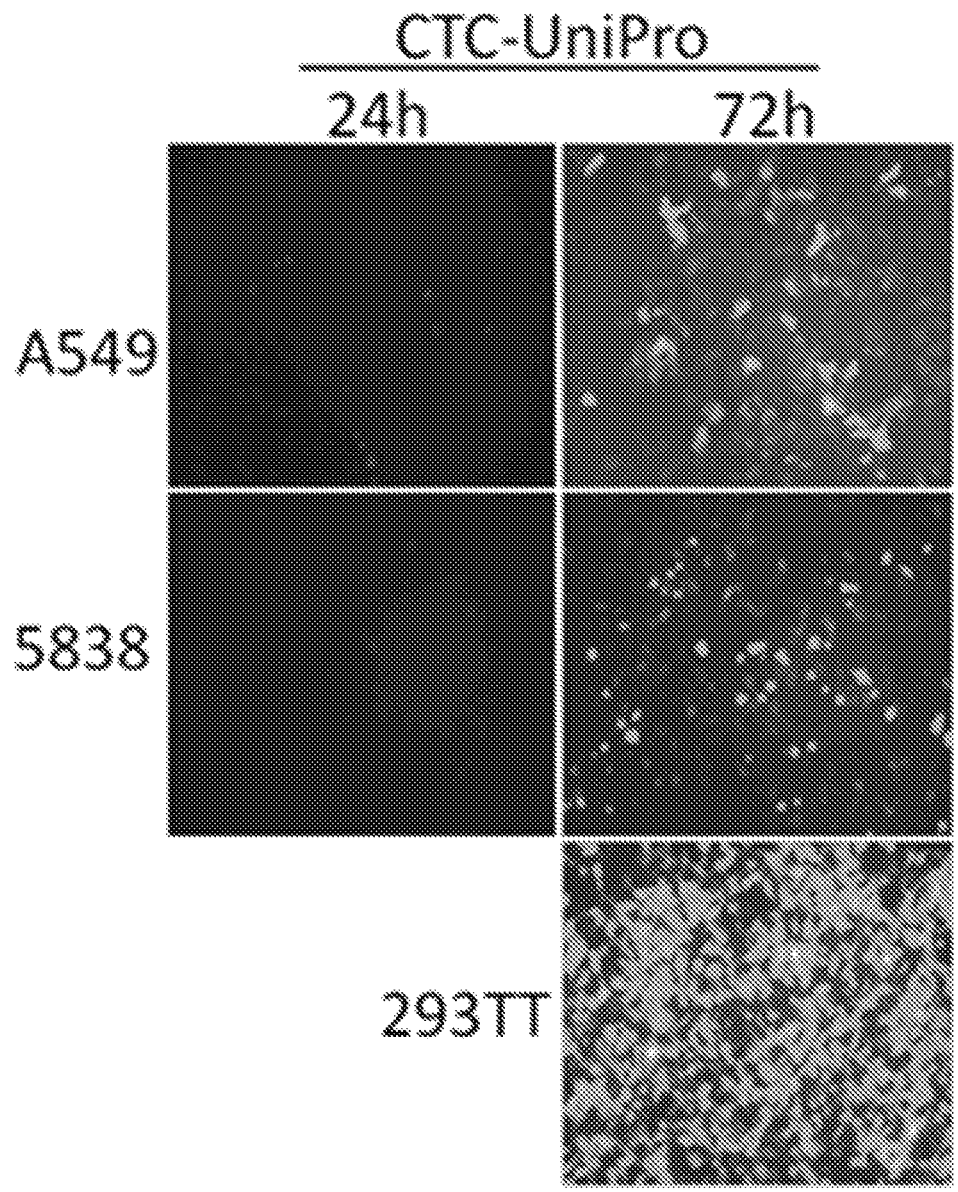
FIG. 3C illustrates detection of human lung cancer cell lines (A549 and 5838) by CTC-UniPro, in accordance with embodiments disclosed herein.

In one embodiment, two human lung cancer cell lines (A549 and 5838) can be incubated with either CTC-UniPro or the pcDNA-GFP control construct. A shown in FIG. 3B, there is a low detection of GFP in wells containing pcDNA-GFP after 24 hours and again after 72 hours. In contrast, as shown in FIG. 3C, there are high levels of GFP in the wells containing CTC-UniPro, indicating significant amplification of the probe. A person of ordinary skill in the art understands that the high amplification is due to the presence of T antigens.

In yet another embodiment, 293TT cells, which express the T antigens necessary for self-amplification, can be incubated with both the pcDNA-GFP construct and CTC-UniPro. By way of example only, FIG. 3B illustrates an increase in GFP expression in the well with pcDNA-GPF and 293TT cells, similar to those seen in FIG. 3C where CTC-UniPro and 293TT cells are used instead. Again, a person of ordinary skill in the art understands that the enhanced detection of GFP by the pcDNA-GFP construct in 293TT cells is due to the addition of T antigens causing self-amplification.

Figure 4:
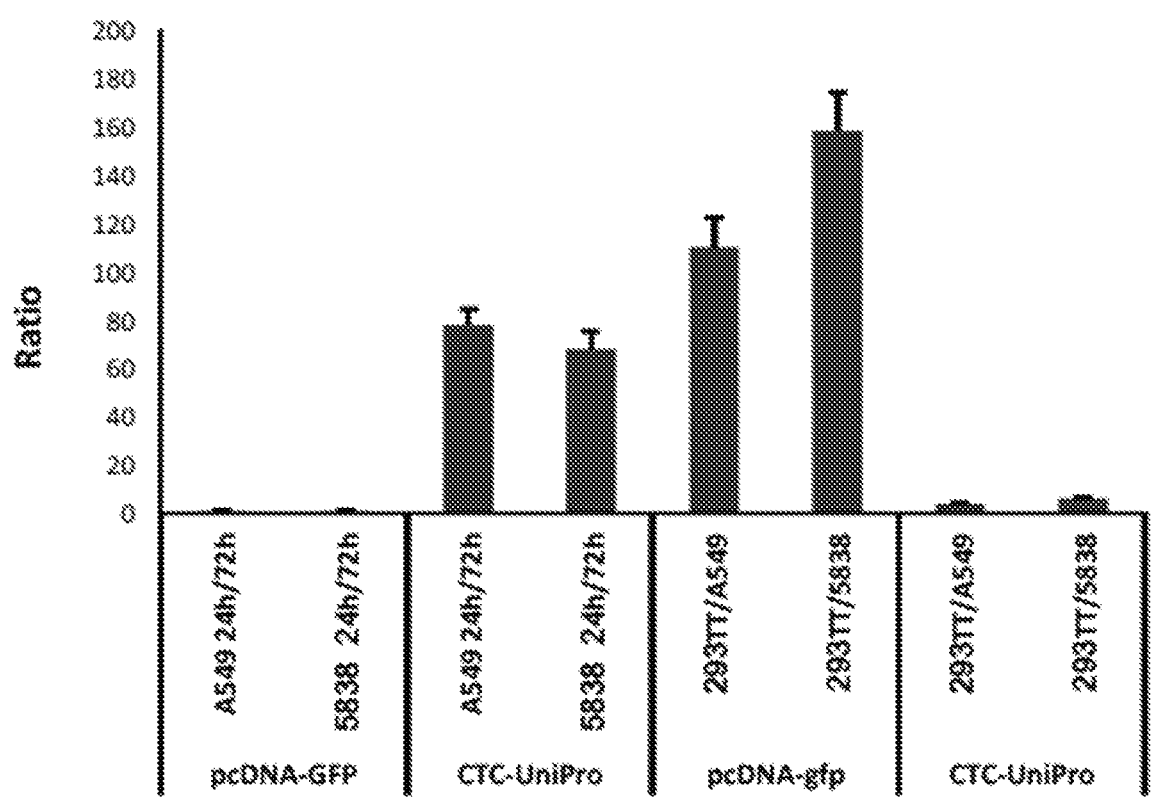
FIG. 4 illustrates a comparison of the quantitative measurement of probe amplification in malignant cells by the pcDNA-GFP control construct versus CTC-UniPro, in accordance with embodiments disclosed herein.

In still another embodiment, a fluorescent illuminator can be used to quantitate GFP expression by CTC-UniPro and the pcDNA-GFP construct, both with and without the addition of 293TT cells, with triplicate wells for each incubation. FIG. 4 illustrates that CTC-UniPro can self-amplify nearly 80 fold after entering CTCs, a significant enhancement of detection sensitivity. The increase in amplification resulting from the T antigens indicates it contains again clearly shows that T antigens are necessary for self-amplification, and that self-amplification can be further improved by manipulation the expression of T antigens.

CTC-UniPro—Detection of a Wide Range of Tumor Cells

Figure 5:
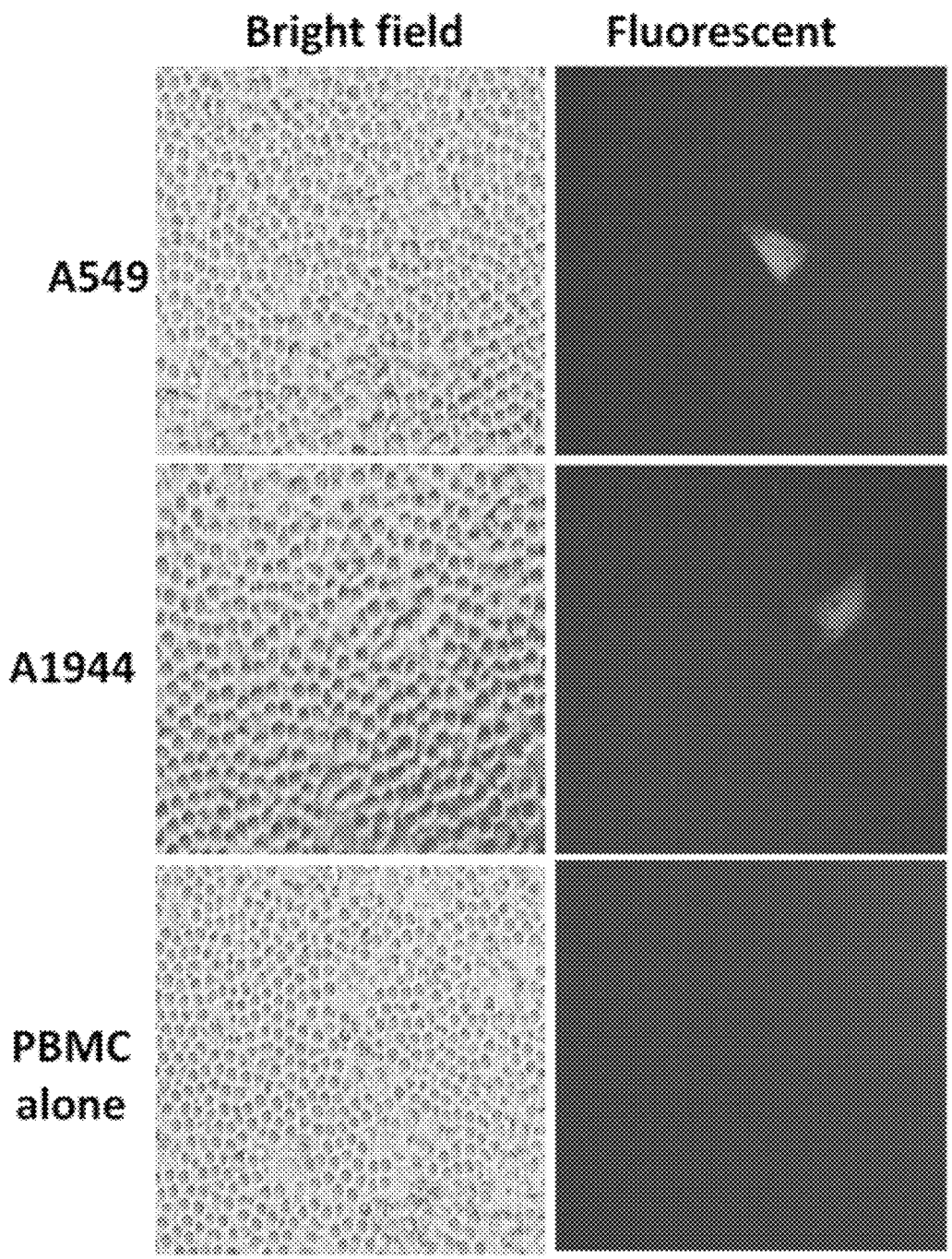
FIG. 5 illustrates a comparison of detection of A549 tumor cells mixed with PBMCs, A1944 tumor cells mixed with PBMCs, and human PMBCs alone, by CTC-UniPro (through GFP identification), in accordance with embodiment disclosed herein.

In an embodiment, the CTC-UniPro described herein can detect a wide range of tumor cells. By way of example only, to determine CTC-UniPro's ability to detect rare CTCs, five million human PBMCs can be mixed with varying numbers of tumor cells and incubated with CTC-UniPro. As shown in FIG. 5, CTCs can be detected by CTC-UniPro, even where the concentration of CTC in PBMCs is as low as 1:5,000,000.

Figure 7:
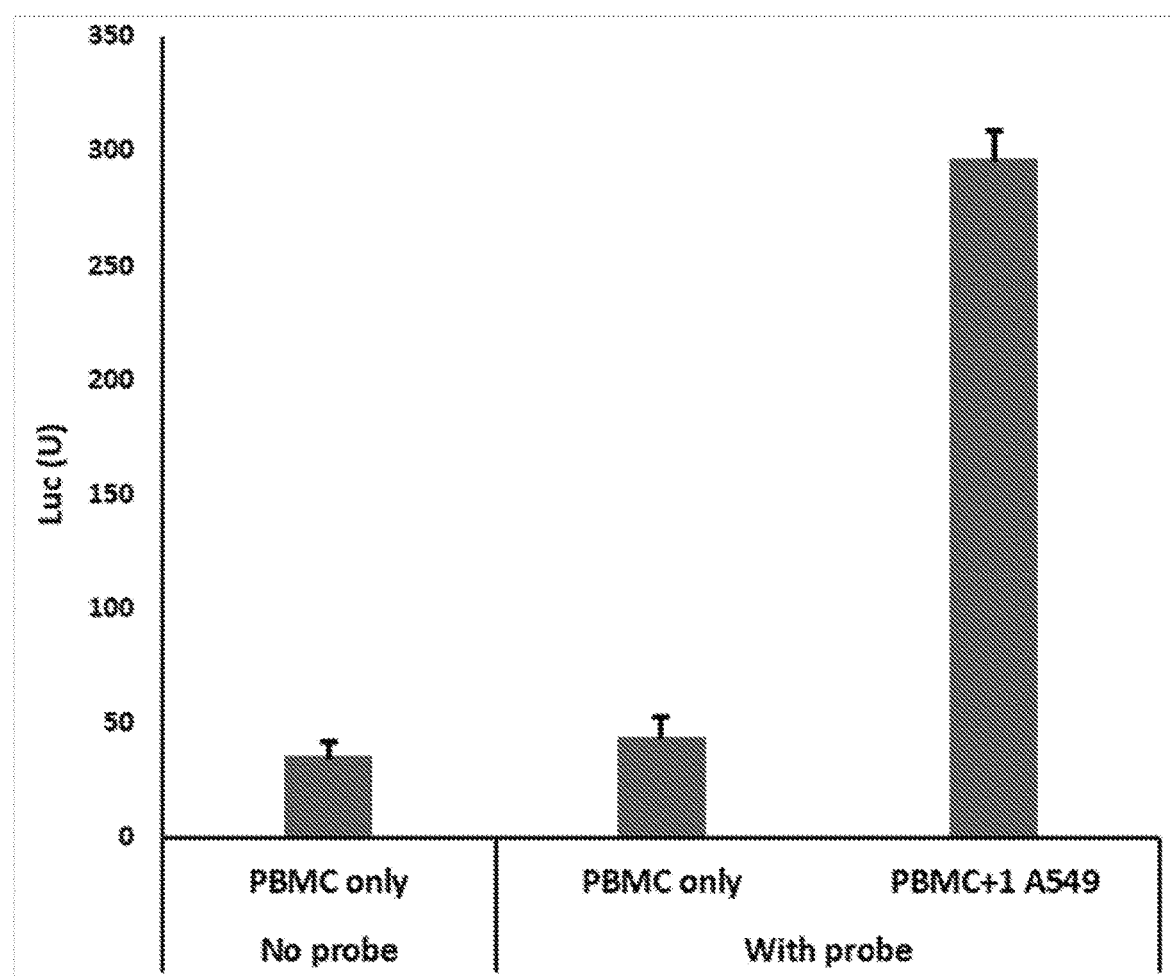
FIG. 7 illustrates the capability of luciferase-containing CTC-UniPro in quantitatively detecting a single tumor cells spiked with $5 \times 10^6$ PBMCs, in accordance with embodiments disclosed herein.

In an embodiment, the CTC-UniPro described herein can quantitatively detect CTCs with extremely high sensitivity. By way of example only, to determine CTC-UniPro's ability to detect rare CTCs, five million human PBMCs can be mixed with varying numbers of tumor cells and incubated with CTC-UniPro. As shown in FIG. 7, CTCs can be detected by CTC-UniPro quantitatively, even where the concentration of CTC in PBMCs is as low as 1:5,000,000.

In another embodiment, the CTC-UniPro described herein can detect CTCs from malignant cells of different tissue origins. By way of example only, PBMCs can be mixed with over 48 types of tumor cells and all of them in the mixture can be readily detected with CTC-UniPro. By way of example only, FIG. 3A, which shows that CTC-UniPro but not pcDNA-GFP can readily detect tumor cells of three different organ tissue origins (H1944 and H358 from lung, Huh-7 from liver and PC-3 from prostate). CTC-UniPro thus has universal capabilities in detecting CTCs from many different tissues (as listed in Table 1).

CTC-UniPro—Comparison with Other Virus-Based Detection Methods

Figure 6:
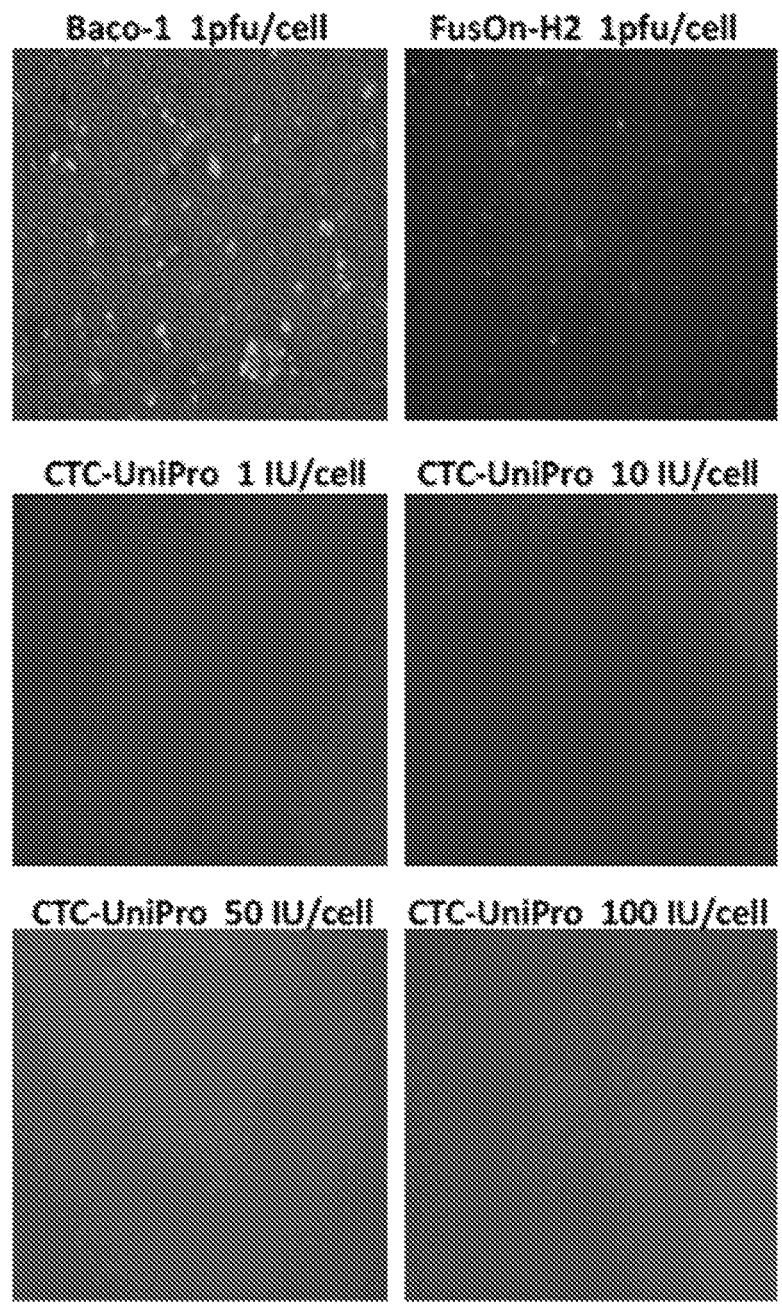
FIG. 6 illustrates a comparison of nonspecific detection of PBMCs by two different oncolytic HSV-based viral vectors (Baco-1 and FusOn-H2), but not by the CTC-UniPro, in accordance with embodiments disclosed herein.

In one embodiment, the CTC-UniPro described herein is capable of detecting CTCs in the blood stream at a higher sensitivity than other detectors. For example, CTC-UniPro is compared to detection of CTCs by an oncolytic herpes simplex virus (HSV), which may detect CTCs, but may also infect normal blood cells, such as lymphocytes, monocytes, and dendritic cells, leading to specificity issues.16-20 Baco-1, derived from HSV-1, and FusOn-H2, derived from HSV-2, contain the GFP gene.[21,22] Human PBMCs can be incubated with either Baco-1, FusOn-H2, or CTC-UniPro. FIG. 6 illustrates GFP detection in the wells containing oncolytic HSVs as early as 24 hours after incubation, and significantly increasing after 72 hours of incubation. In comparison, no GFP positive cells were detected after 72 hours in the wells containing CTC-UniPro. If oncolytic HSVs were used for detecting CTCs, they would result in significant false positive diagnoses. Additionally, HSV can destroy CTCs in a short amount of time, due to its cytolytic nature, causing inaccurate quantitation of CTCs and eliminating the possibility of subsequent harvesting of CTCs.

CTC-UniPro has an extremely high specificity for CTCs, due to HPV-16's ability to infect epithelial cells only.[23] This is because in the clinical setting, blood will be drawn from cancer patients from which PBMCs will be isolated. As the PBMCs are not epithelial origin, thus they can not be detected (i.e., infected) by CTC-UniPro (e.g., as demonstrated in FIG. 3A). The only cells that can be detected by CTC-UniPro will be the CTCs contained in the PBMCs.

In one embodiment, the blood of a cancer patient is collected. PBMCs are separated from the blood, and then the PBMCs are mixed with tumor cells at different ratios before detection by a CTC-Unipro described herein. CTCs can then be detected using the CTC-Unipro, which, for example, can identify the CTCs by showing them as green color (e.g., FIG. 5).

Cell lines and viruses for construction of CTC-UniPro. The 293TT cell line was obtained from National Cancer Institute. Lung cancer cell lines A549, H1944, 5838 and H358, and African green monkey kidney (Vero) cells were obtained from American Type Culture Collection (Rockville, MD). 293TT cells were cultured in DMEM (GE Healthcare Life Sciences HyClone Laboratories South Logan, Utah) supplemented with 10% fetal bovine serum (FBS, Mediatech, Manassas, VA), 100 units/mL penicillin, and 100 µg/mL streptomycin, 1% non-essential amino acids, and 1% Glutamax (Thermo Fisher Scientific, Waltham, MA). Other cells were cultured in DMEM containing 10% FBS. All cells were incubated at 37° C. in a humidified atmosphere with 5% $CO_2$. Type I herpes simplex virus (HSV-1) based oncolytic virus Baco-1 and HSV-2 based FusOn-H2 were originally constructed in the University of Houston Department of Biology and Biochemistry Laboratory. Both viruses contain the GFP gene and thus their infection can be readily identifiable by the appearance of green fluorescent cells or plaques. They were grown and titrated on Vero cells as described herein. A Luc gene, instead of the GFP, may allow for more accurate quantitative measurement. A membrane protein containing a tag, such as a HA tag, may allow for easy subsequent harvest of CTCs through the use of anti-HA antibody conjugated magnetic beads.

Preparation and purification of CTC-UniPro and the control vector. The details of the construction strategy are illustrated in FIG. 1A-FIG. 1C. CTC-UniPro contains two key components: a specified CTC diagnostic probe (pSV-GFP) (FIG. 1A) and a packaging system (pHPV1,2) (FIG. 1B) that would allow the probe to enter CTC for subsequent amplification and detection. As shown in FIG. 1A, the pSV-GFP was designed based on the wild type (wt) SV40 genome with several modifications. Initially, the entire VP 1-3 capsid genes from nucleotides (nt) 371 to 2532 along the SV40 genome was deleted and replaced with the GFP gene. As the deleted region contains the natural polyA signal, a synthetic polyA was inserted back to the end of the GFP gene. In order to enhance GFP expression, three modifications were made to the SV40 late promoter region. First, an additional 4 copies of the 72 base pair repeats were added downstream of the natural 21 base pair repeat and 2×72 base pair repeats to strengthen the late promoter. Second, a series of mutations were introduced to the late promoter, which include: C to T at nucleotide 298, 299, 304 and G to C at nucleotide 322 and A to C at nucleotide 335. The packaging construct, pHPVL1,2, was constructed by synthesizing both the L1 and L2 genes based on sequences from human papillomavirus (HPV) 16. These two genes are separated by a 2A sequence.

The above-mentioned modifications were done through DNA synthesis with codon optimization for human cell expression, and the synthesis was done by GenScript (Piscataway, N.J.). The control vector was derived from pcDNA-GFP (FIG. 1C). It contained a copy of the SV40 Ori-P sequence as well as a GFP cassette in which the marker gene was driven by the CMV promoter. For production of CTC-UniPro and the control vector, 293TT cells were plated in a 10 cm dish 16 hours prior to transfection. Plasmid pHPVL1,2 was mixed with either pSV-GFP or pCDNA-GFP, and the mixtures were then co-transfected into the 293TT cells using Lipofectamine 2000 (Thermo Fisher). From these cotransfections, the L1 and L2 expressed from pHAV1,2 formed virus like particles (VLPs), which could then package the probe (pSV-GFP) or the control vector (pcDNA-GFP). The transfected cells were harvested at 48 or 72 hours after transfection. Cell pellets were washed once with PBS before they were suspended and lysed with the lysis buffer: phosphate buffered saline (PBS) supplemented with 9.5 mM $MgCl_2$ (Sigma®, St. Louis, Mo.), 0.5% Triton 100 (Thermo Fisher), and 0.1% Benzonase (Sigma®) and 25 mM NH4SO4 (pH 9) to release the probe. The lysates were incubated for 24 hours at 37° C. to allow the VLPs to mature before 5 M NaCl was added to make the final concentration 850 mM. The lysates were briefly chilled on ice before they were centrifuged at 5,000 g for 5 minutes at 4° C. The clarified probes were further purified with GE Capto Core 700 and DP-10 columns (GE Healthcare Bio-Sciences, Pittsburgh, Pa.) following the manufacturer's protocols. The purified probes were quantitated by incubating a small aliquot with 293TT cells for 48 hours. GFP positive cells were confirmed by a fluorescence microscope (Nikon Instruments Inc. Melville, N.Y.) and quantitated by flow cytometry (BD Biosciences, San Jose, Calif.).

Human PBMC preparation. Human peripheral blood mononuclear cells (PBMC's) were prepared from buffy coats obtained from Gulf Coast Regional Blood Center (Houston, Tex.). The buffy coats were mixed with an equal amount of PBS before they were loaded on Lymphoprep (STEMCELL Technologies, Vancouver, BC, Canada) for centrifugation for 30 minutes at 800 g with brake off at room temperature. PBMCs were collected from the layer at the plasma: Lymphoprep interface and were washed twice with 2% FBS-PBS. The cell pellets were treated with red blood cell lysing buffer (Sigma®) to remove red blood cells and were washed again twice with 2% FBS-PBS. The purified PBMCs were used directly for the experiments.

Tumor cell detection by the probes. For testing the ability of CTC-UniPro to amplify in tumor cells, $1-2\times10^5$ tumor cells of different tissue origins were plated in 12 or 24 well plates overnight. Cells were then incubated with either CTC-UniPro or the control vector at 2 infection units (IUs) per cell for 24 to 96 hours depending on each individual experiment. Cells were then analyzed under a fluorescence microscope. To mimic the situation of clinical diagnosis, 10 or 100 cancer cells were mixed with $2\times10^6$ PBMCs in RPMI 1640 plus 10% FBS in 12 well plates. The mixed cells or PBMCs alone were incubated with $1\times10^7$ IU of CTC-UniPro at 37° C. for 72 hours. For testing the ability of oncolytic herpes simplex virus to infect PBMCs, cells were infected with either Baco-1 or FusOn-H2 at 1 pfu for 72 hours.

GFP quantification. To quantitatively measure the probe intensity in cancer cells, the indicated cells were incubated with either CTC-UniPro or the control vector at 2 IU. The cells were harvested at 72 hours later. The quantitative measurement of GFP was performed with GFP Quantification Kit (BioVision®, Milpitas, Calif.). Briefly, the harvested cells were lysed with assay buffer for 10 minutes. The supernatants were cleared by centrifugation before they were transferred to a 96 well plate. The samples were quantitated on a fluorescence microplate reader (Victor™ X4, PerkinElmer, Akron, Ohio).

---

The invention claimed is:

1. A probe for detecting circulating tumor cells (CTCs), comprising:
a modified SV40 viral genome packaged into a capsid formed from the L1 and L2 capsid proteins of a human, bovine, or other papillomavirus, and including the luciferase (luc) marker gene of SEQ ID NO: 10, wherein the modified SV40 viral genome also comprises an SV40 virus late promoter.

2. The probe of claim 1, wherein the marker gene is inserted into the modified SV40 viral genome downstream of the SV40 virus late promoter.

3. The probe of claim 1, wherein the SV40 virus late promoter is modified by eliminating the endogenous start codon.

4. The probe of claim 1, wherein the SV40 viral genome is modified by inserting four 72 tandem repeat enhancer sequences.

5. The probe of claim 1, wherein the SV40 viral genome is modified by one or more of the following: substituting nucleotide 298 from cytosine (C) to thymine (T), substituting nucleotide 299 from C to T, substituting nucleotide 304 from C to T, and substituting nucleotide 322 from guanine (G) to C, wherein the nucleotide positions of 289, 299, 304, and 322 correspond to 671, 672, 677, and 695, respectively, of SEQ ID NO: 1.

6. A process for assembling a probe that can detect circulating tumor cells (CTCs), the process comprising:
co-transfecting papilloma virus L1 and L2 genes with a modified SV40 viral genome construct into mammalian cells, or by in vitro assembly of the modified SV40 viral genome construct into capsids formed from co-transfecting the papilloma virus L1 and L2 genes into mammalian cells;
wherein the probe includes the luciferase marker gene of SEQ ID NO: 10; and
wherein the modified SV40 viral genome also comprises an SV40 virus late promoter.

7. The process of claim 6, wherein the co-transfecting comprises co-transfecting pSV-GFP and pHPVL1,2 into 293TT cells.

8. The process of claim 6, wherein the mammalian cells are 293TT cells.

9. The process of claim 6, wherein the SV40 virus late promoter is modified by eliminating the endogenous start codon.

10. The process of claim 6, wherein the SV40 viral genome construct is modified by inserting four 72 tandem repeat enhancer sequences.

11. The process of claim 6, wherein the SV40 viral genome construct is modified by one or more of the following:

substituting nucleotide 298 from cytosine (C) to thymine (T), substituting nucleotide 299 from C to T, substituting nucleotide 304 from C to T, and substituting nucleotide 322 from guanine (G) to C, wherein the nucleotide positions of 289, 299, 304, and 322 correspond to 671, 672, 677, and 695, respectively, of SEQ ID NO: 1.

12. A method for detecting circulating tumor cells (CTCs) in a patient using a probe, the method comprising:
collecting blood from a patient;
isolating nucleated cells from the blood;
preparing a mixture that includes the isolated nucleated cells from the blood and a probe for detecting CTCs, wherein the probe comprises a modified SV40 viral genome having a SV40 virus late promoter, a modified capsid formed from the L1 and L2 capsid proteins of a papillomavirus, and containing the luciferase (luc) marker gene of SEQ ID NO: 10; and
detecting CTCs in the mixture.

13. The method of claim 12, wherein the nucleated cells include peripheral blood mononuclear cells (PBMCs) or CTCs.

14. The method of claim 12, wherein the SV40 viral genome is modified by one or more of (i) eliminating the endogenous start codon of SV40, (ii) inserting four 72 tandem repeat enhancer sequences into SV40, and (iii) substituting nucleotide 298 from cytosine (C) to thymine (T) in SV40, (iv) substituting nucleotide 299 from cytosine to thymine in SV40, (v) substituting nucleotide 304 from cytosine to thymine in SV40, and (vi) substituting nucleotide 322 from guanine (G) to C in SV40, wherein the nucleotide positions of 289, 299, 304, and 322 correspond to 671, 672, 677, and 695, respectively, of SEQ ID NO: 1.

* * * * *